(12) United States Patent
Corbin et al.

(10) Patent No.: US 6,748,834 B2
(45) Date of Patent: Jun. 15, 2004

(54) SUPER FINISHING OF POLYMERIC IMPLANT COMPONENTS

(75) Inventors: Dexter Corbin, Fareham (GB); Pierre S. Ostiguy, Hampshire, MA (US)

(73) Assignee: Johnson & Johnson Professional, Inc., Raynham, MA (US)

( * ) Notice: Subject to any disclaimer, the term of this patent is extended or adjusted under 35 U.S.C. 154(b) by 32 days.

(21) Appl. No.: 09/934,132

(22) Filed: Aug. 20, 2001

(65) Prior Publication Data

US 2001/0054224 A1 Dec. 27, 2001

Related U.S. Application Data

(62) Division of application No. 09/193,335, filed on Aug. 18, 2000.

(51) Int. Cl.[7] ............ B23B 3/00; A61B 19/00; A61F 2/28
(52) U.S. Cl. ............ 82/1.11; 82/118; 128/898; 623/23.58
(58) Field of Search ............ 82/1.11, 118, 120, 82/121; 407/118, 119; 264/162; 128/898; 623/23-58

(56) References Cited

U.S. PATENT DOCUMENTS

| | | | |
|---|---|---|---|
| 4,434,581 A | * | 3/1984 | Spriggs ............ 451/173 |
| 4,673,408 A | | 6/1987 | Grobbelaar |
| 4,687,487 A | | 8/1987 | Hintermann |
| 4,760,672 A | | 8/1988 | Darcangelo et al. |
| 4,795,472 A | | 1/1989 | Crowninshield |
| 4,901,480 A | | 2/1990 | Dillon |
| 4,908,997 A | | 3/1990 | Field, Jr. et al. |
| 4,946,318 A | * | 8/1990 | David et al. ............ 407/42 |
| 5,149,337 A | | 9/1992 | Watanabe |
| 5,171,275 A | | 12/1992 | Ling et al. |
| 5,310,408 A | | 5/1994 | Schryver et al. |
| 5,326,376 A | | 7/1994 | Warner et al. |
| 5,410,843 A | | 5/1995 | Gottschald |
| 5,458,819 A | * | 10/1995 | Chirila et al. ............ 264/1.7 |
| 5,463,503 A | | 10/1995 | Kawada et al. |
| 5,593,445 A | | 1/1997 | Waits |
| 5,593,452 A | | 1/1997 | Higham et al. |
| 5,593,719 A | | 1/1997 | Dearnaley et al. |
| 5,702,448 A | | 12/1997 | Buechel et al. |
| 5,802,937 A | * | 9/1998 | Day et al. ............ 82/1.11 |
| 6,059,830 A | * | 5/2000 | Lippincott, III et al. . 623/18.11 |
| 6,488,654 B2 | * | 12/2002 | Gonzalez et al. ...... 604/103.06 |

FOREIGN PATENT DOCUMENTS

| | | |
|---|---|---|
| DE | 4343183 A1 | 6/1994 |
| WO | WO 97/31592 | 9/1997 |

OTHER PUBLICATIONS

Contour Fine Tooling, Ltd., "Controlling Waviness Contact Lens Tools," product brochure.
Precitech, Inc., "Accessory Equipment," product brochure (revised Feb. 17, 1998).
Precitech, Inc., "NANOFORM 200," product brochure (revised Feb. 2, 1998).
Precitech, Inc., "NANOFORM 200," product brochure.

* cited by examiner

*Primary Examiner*—A. L. Wellington
*Assistant Examiner*—Brian D. Walsh
(74) *Attorney, Agent, or Firm*—Nutter McClennen & Fish LLP

(57) ABSTRACT

A method for preparing a contact surface of an implantable bone, joint or similar prosthetic component subject to contact or motion includes the steps of mounting the prosthetic component on a turning or cutting machine and cutting the face of the prosthetic component with a diamond cutting tool using computerized control of tool position along a cross direction to machine cut a super finished surface. The variations of contour and the surface roughness are both under about 0.5 micrometers, and preferably under about 0.2 micrometers or less. The super finished surface generates wear particles at an asymptotically low or residual level during wear-in which may enhance wear characteristics and reduce local reaction or systemic rejection effects. The component is preferably formed by a strong hard polymer, such as UHMWPE.

14 Claims, 5 Drawing Sheets

SUPER FINISHING OF POLYMERIC IMPLANT COMPONENTS

CROSS-REFERENCE TO RELATED APPLICATIONS

This application is a Divisional of U.S. patent application Ser. No. 09/193,335, filed on Aug. 18, 2000, and is hereby incorporated by reference in its entirety.

STATEMENTS REGARDING FEDERALLY SPONSORED RESEARCH

Not Applicable.

FIELD OF THE INVENTION

The invention relates generally to the surface finishing of implantable prosthetic components. More particularly, the invention relates to surface finishing of an articulating or contacting surface of a polymeric orthopedic prosthesis.

BACKGROUND OF THE INVENTION

Those in the art have generally utilized, in conjunction with prosthetic implantation surgeries, components that have varying surface roughness characteristics. For example, it is currently common in the art for components such as liners, cups, stems, heads, trays and shells to be implanted in a human body with polished or as-machined surface finishes wherein machine lines or feed lines on the component(s) are visible to the unaided eye. These surface texture or roughness characteristics tend to produce wear debris that is shed from the components during a "breaking-in" or "wearing-in" period that occurs due to, for example, micromotion at a shell to liner interface, or due to articulation at a liner to head interface.

When quantities of wear debris are generated and accumulate in an implanted prosthesis, problems may arise that compromise the longevity and/or integrity of the implanted component(s) or the entire implanted prosthesis. Among these problems is the possibility of a component or components becoming loosened which, in turn, could render the component(s) or the entire prosthesis ineffective for its intended purpose, or which could cause fracture of the affected implanted component(s) or prosthesis. Other problems which could occur are local inflammation or tissue reactions, or the resorption of the bone(s) surrounding, or in the vicinity of, the implanted prosthesis. Such bone resorption could, in turn, prematurely necessitate the total replacement of the entire prosthesis via revision surgery.

Several previous attempts have been made to limit the amount of wear debris produced as a result of the "breaking in" or "wearing-in" of components due to, among other things, micromotion and/or articulation. These attempts have focused on attempting to produce components with higher quality finishes that have less surface roughness. For example, some in the art have performed supplemental hot pressing of the polymeric components to be used in connection with prosthetic implantation surgeries in order to improve the surface finish of those components. Such supplemental hot pressing, however, has detrimental effects on the microstructure of the pressed components, and may cause delamination of articulating surfaces of ultra-high molecular weight polyethylene implantation components. Other approaches in the art have either not been able to produce components with higher quality finishes or have produced such components only with accompanying drawbacks to the performance and/or structure of the components.

Therefore, a need exists in the art for non-specialized components that have improved finishes for use in prosthetic implantation surgeries. In particular, there is a need for finished components that have a surface that reduces or substantially eliminates the formation of wear debris when the surface is subjected to contact or motion, while not adversely affecting the microstructure of the components, and which otherwise maintains beneficial aspects of prior art implantation components. A need also exists for a method to prepare such components.

BRIEF SUMMARY OF THE INVENTION

This invention provides a finished implantable polymeric prosthetic joint or bone component having a superior surface finish, or "super finish", and a method for fabricating the component. The joint or bone component can be a cup, shell, tray insert, stem, liner or head, or other component which has a face that, once implanted or during implantation, is a surface which is to be subjected to a surface-to-surface contact, or motion. The joint or bone component is prepared by subjecting the component to a turning movement against a surface cutting tool such that the component has a circularly symmetric or radially symmetric finish region with an as-machined cut surface finish substantially smoother than about 0.5 micrometers. The joint or bone component, once prepared in accordance with the present invention, has a visually smooth contact region and is matable with a similarly contoured implant component for sliding or micromovement therebetween.

In an alternate embodiment of the invention, the implantable polymeric prosthetic joint or bone component has a two-dimensional surface contour with an as-machined surface profile in a cross direction with peak to valley surface smoothness effective to achieve in vivo particle generation at a residual (e.g., asymptotically flat) level or rate.

Also provided by the present invention is a method of preparing the implantable prosthetic joint or bone component. The method comprises the steps of placing the component in a mounting, such as a chuck or collet, on a turning machine, such as a lathe, for rotation against a replaceable or resharpenable cutting tool, and rotationally cutting the face of the component with a diamond cutting tool having a predetermined shape, geometry and sharpness effective to form a cut surface contour with waviness under 0.5 micrometers. The cutting tool may be brazed into a tool tip insert such as a steel or carbide tip insert, or clamped onto a tool holder for indexable tooling.

Preferably, once mounted, the component is rotated while the cutting tool is fed across a controlled R, X & Z feed path one or more times, with each time constituting one "pass." Each pass removes material from the surface of the component, and the diamond cutter tool path forms a final profile. During the turning of the component by the cutting tool, the position of the cutting tool and/or the total number of passes of the cutting tool may be controlled by computer. The method of the present invention also contemplates steps of cooling the cutting edge of the tool and/or removing swarf while the cutting of the component occurs. The method concludes when the surface attains the desired shape, with a surface finish substantially smoother than 0.5 micrometers and a variation of contour waviness less than or equal to 0.5 micrometers. The method of the present invention preferably provides a smooth surface finish with excursions or variations from a nominal flat or curved surface profile lying below a threshold which is 0.05 and 0.10 micrometers.

In an alternate embodiment of the method of preparing the implantable prosthetic joint or bone component, the cutting tool may be rotated to fly cut a surface of the component while it is held stationary or translated. In still further embodiments, the turning machine carries the component on an air-bearing, and the tool compound may operate with air or hydrostatic slides and damping to minimize vibration, or to prevent transfer of vibrational artifacts to the surface finish of the component.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
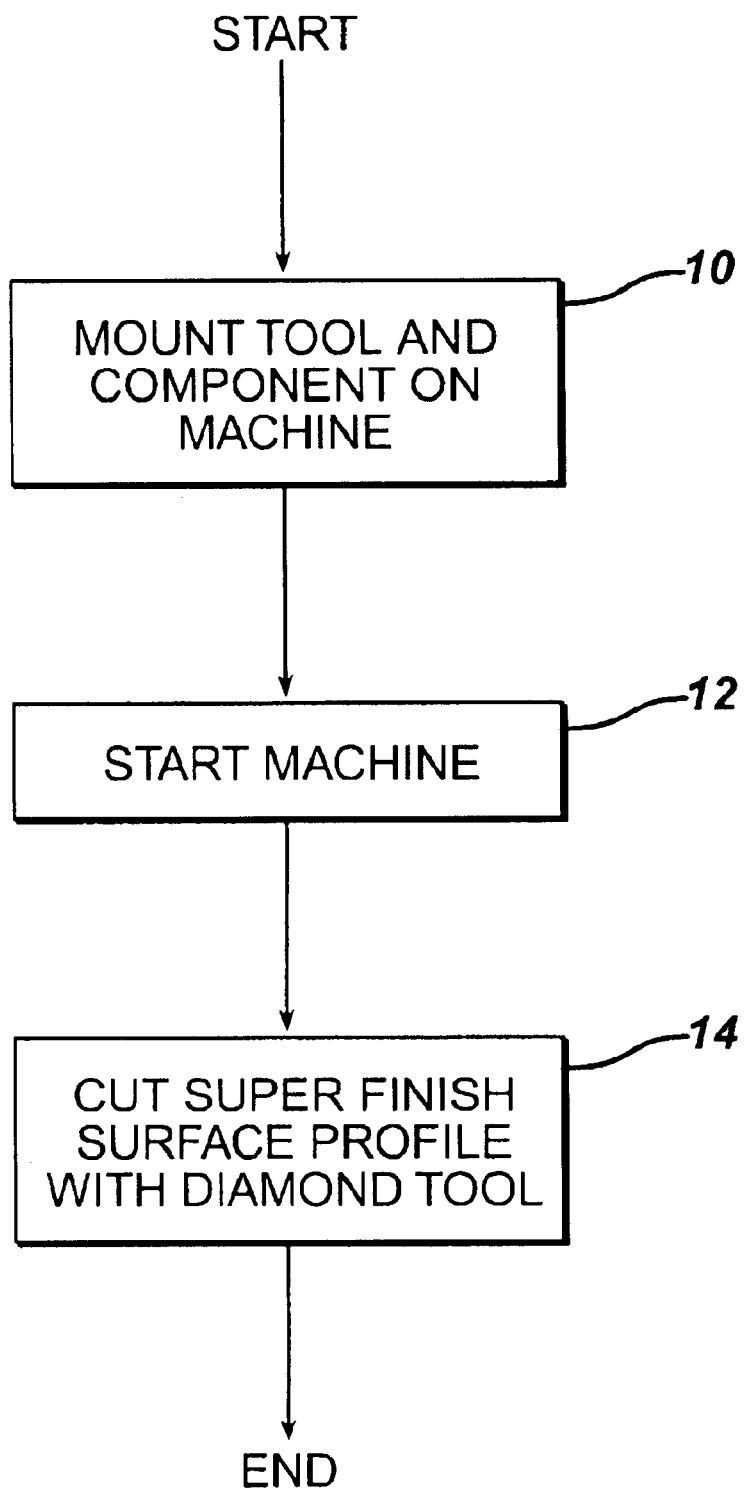
FIG. 1 is a flow diagram illustrating the steps of a process for preparing an implant component in accordance with the present invention.

A process for preparing an implant component in accordance with the present invention is shown in the flow diagram of FIG. 1. For the first step 10 of the process, an implant component is mounted on a machine such as a turning lathe. Suitable implant components for mounting include a joint or bone prosthesis component such as a cup, shell, tray, stem, liner or head or any other implant component which has a face that possesses radial symmetry in a region, and that is a flat or curved surface which is to be subjected to contact or motion once implanted or during implantation. Particularly suitable implant components are those made of ultra-high molecular weight polyethylene (UHMWPE) and include, but are not limited to, acetabular liners for hip prostheses and tibial trays, stems of tibial plateaus for knee prostheses.

Suitable turning machines include horizontal or vertical lathes and, in particular, a horizontal, chucking-type turret lathe which accommodates one or more surface cutting tools. Milling machines or mill/turning machines may also be used for the practice of the invention. The machine may be adapted to operate with air bearings to move effectively isolate the implant component from mechanical vibration during the machining process. Preferably, a turning machine is used that is adapted with air bearings and allows for a positioning tolerance of within 0.005 millimeters, with an electronic feed with ball screws to effectively eliminate backlash.

The implant component is mounted via means capable of firmly grasping and holding, but not deforming, implant components that are made of various materials and have various dimensions. Some of the suitable means for mounting the implant component include a collet or a chuck, which is preferably formed with a receiving shape closely adapted to be the outside profile of the component, and which may be configured for vacuum clamping in a production setting. The means for mounting the implant component may be operated via manual or automated control. On a lathe, the implant component is mounted on the turning axis of the machine while on a fly cutter, it is mounted along the axis of the tool movement.

Once the implant component is mounted in accordance with the first step 10 of the process of FIG. 1, the process continues to the second step 12. During the second step 12 of the process, the component comes into rotational contact with a cutting tool or tools. The contacting of the cutting tool(s) and the component may be accomplished several ways, including, but not limited to, rotating the component and feeding the tool against the component or rotating the cutting tool(s) to fly cut a component which is held stationary or translated.

The cutting tool(s) of the turning machine should be made of material(s), and should have a shape, a geometry and a sharpness, and should be rotated at a rate sufficient to achieve the aforesaid surface profile and surface finish for the component being cut. Generally, applicant has found a single diamond tool to suffice for the finish cut and for rough cuts if any of these are necessary. However, more cutting tools may be provided, and if more than one cutting tool is provided, these may include tools of high speed steel, carbide or the like for rough cutting. In any event, the final tool is a natural or synthetic diamond cutting tool. The diamond cutting tool may be brazed into a tool tip insert such as a steel or carbide insert. The cutting tool(s) should either be resharpenable or replaceable after a predetermined number of cuts or a predetermined amount of cutting time or when the tools(s) have achieved a predetermined level of dullness, and may be adapted to be easily retrofitted into existing turning machines.

The diamond cutting tools for use in the present invention have sharpness and radii of the cutting edge that allow removal of up to ten or twenty mils in a pass while minimizing the appearance of feed lines on the cut component. Each carbide cutting tool that is provided should have a sharp profile and a cutting radius. Moreover, the sharpness and radius of each of the cutting tools may differ from the other cutting tools, with the sharpnesses being effective to form one or more rough cuts to finish the component sufficiently to allow the diamond to cut the profile in a single pass. In practice, the rough and finish cuts may both be performed with the diamond tool. The cutting tool(s) or the component, whichever is being rotated, should be rotated at a rate over 1000 revolutions per minute, and is preferably rotated at 3500 revolutions per minute or more, with an effective cross feed rate.

The third step 14 of the process is the cutting and shaping of the component by advancing the cutting tool(s) to form the desired surface profile. When the component is rotated, the cutting tool(s) are fed across a multi-axis, controlled feed path a predetermined number of times (with each time constituting one "pass") in order to remove material from the surface of the component so as to achieve a final, predetermined surface profile on the component. Depending on such factors as the material from which the component is made and the geometry of the component, the amount of material removed may vary. Generally, for cutting a quasi-spherical surface, the feed path is an R, X & Z feed path. The tool cross feed is slow, and the amount of time that elapses for cutting a quasi-spherical surface, or for the final cutting tool to complete its feed path, per pass, is about one minute, but may be set to be more or less time via numerical control. It should also be mentioned that manual or CNC-controlled R-θ type machines may also be employed. In this case, the tool may pivot in an arc to form the desired surface contour rather than interpolating the profile as a series of steps.

In order to provide a component with a surface finish that will significantly reduce or eliminate the formation of wear debris while not adversely affecting the microstructure of the component, the component is preferably cut so as to have a surface finish substantially free of tool marks visible to the unaided eye, for example, wherein the surface waviness of the component is under about 0.5 micrometers. The surface finish or roughness of the component should be substantially smoother than 0.5 micrometers, and is preferably a surface smoothness of approximately 0.05 to 0.10 micrometers.

Such surface waviness and surface roughness characteristics may be attained by providing numerical control of the position of the cutting tool, and, if necessary, augmenting the total number of passes the cutting tool makes on the component. The numerical control is provided by computer in a way known in the art.

Furthermore, although a component may be cut by one or more carbide tools and a diamond cutting tool, or by only a diamond tool in accordance with the process of FIG. 1, the diamond cutting tool should always be the last of the tools to contact the face of the component in order to provide the desired low surface roughness and waviness characteristics.

The third step 14 of the process may also include vacuum and/or cooling systems, for example, to cool the cutting surface and/or to remove swarf that accumulates during the cutting process. These vacuum and cooling systems are adapted to perform in conjunction with the cutting tool(s) and the turning machine in ways generally known in the art.

In an alternate embodiment of the invention, an implantable polymeric prosthetic joint or bone component is so as to have a two-dimensional surface contour with an as-machined surface profile in a cross direction with peak to valley surface smoothness effective to achieve in vivo particle generation at a residual level. That is, when placed in use, a moving component generates wear particles due to small irregularities of the opposing surfaces rubbing against each other. Typically, such particles are initially generated at a high rate, primarily from the irregularities of the polymeric components, and as the surfaces become more regular or better fitting, wear particles are generated at a lower or residual rate, which may approach a low or zero level. The present invention achieves this residual level with an as-machined surface of the polymeric component.

Figure 2:
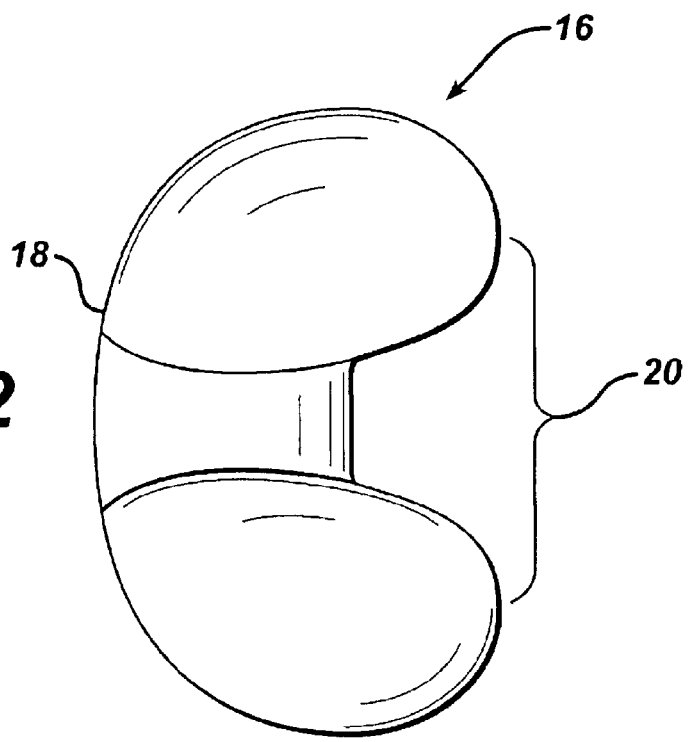
FIG. 2 is a plan view of a tibial insert.
Figure 2A:
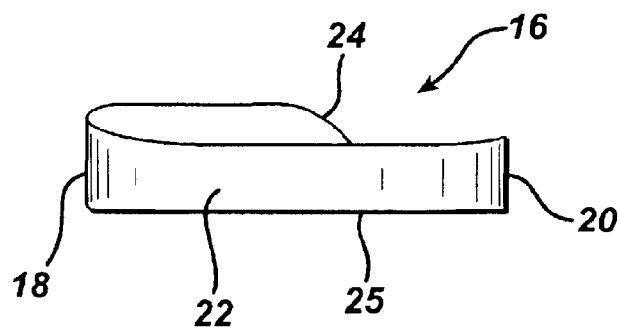
FIG. 2A is a side view of the insert of FIG. 2.
Figure 3:
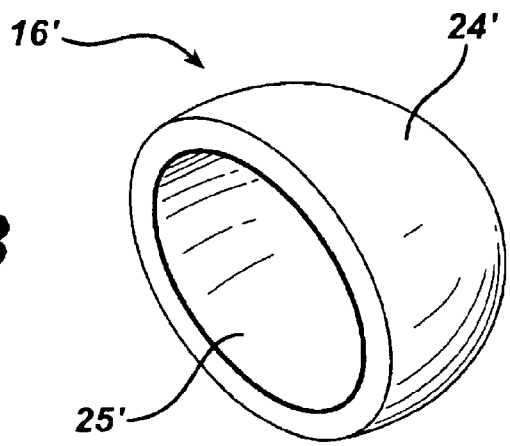
FIG. 3 is a perspective view of a liner.

Referring now to FIGS. 2, 2A and 3, two exemplary implant components that may be prepared in accordance with the three-step process of FIG. 1 are shown. The exemplary component 16 of FIGS. 2 and 2A is an insert for a tibial tray and the exemplary component 16' of FIG. 3 is a liner for an acetabular component. Other implant components that may be prepared in accordance with the process of FIG. 1 include a joint or bone component such as a cup, shell, tray, stem, or head or any other implant component which has a face that, once implanted or during implantation, is a flat or curved surface which is to be subjected to contact or motion, including micro-motion such as that which occurs between nominally stationary, but contacting surfaces. In a preferred embodiment of the present invention, implant components prepared in accordance with the process of FIG. 1 are made of ultra-high molecular weight polyethylene (UHMWPE).

The insert 16 has an anterior surface 18 and a posterior surface 20 and also has medial and lateral surfaces or sides such as 22. The implant has a superior face 24 of curved aspect that will be subjected to contact or motion when utilized in ways known in the art during, and subsequent to, the implantation of a hip prosthesis, and that face may be super finished in accordance with the process of FIG. 1 such that the face has a surface finish substantially free of tool mark waviness visible to the unaided eye wherein its surface waviness is under about 0.5 micrometers and its surface finish has a surface roughness substantially less than 0.5 micrometers, preferably less than approximately 0.05 to 0.10 micrometers. Similarly, an interior surface 25 of the insert 16 may be fly cut to a flat non-wavy super finished profile.

The liner 16' is a concave shell of bearing material having an interior face 25' and an exterior surface 24'. As is generally known to those in the art, the liner 16' fits within a generally metallic external support or acetabular component (not shown), while a ball of a corresponding femoral component of the prosthesis (not shown) bears against the interior surface 25' of the liner. The interior and exterior surfaces 25', 24' of the liner 16' will be subjected to contact or motion when utilized in ways known in the art during, and subsequent to, the implantation of a hip prosthesis, and these faces may be super finished in accordance with the process of FIG. 1 such that the faces have a surface finish substantially free of tool mark waviness visible to the unaided eye wherein its surface waviness is under about 0.5 micrometers and its surface finish has a surface roughness substantially less than 0.5 micrometers, preferably less than approximately 0.05 to 0.10 micrometers.

Figure 4:
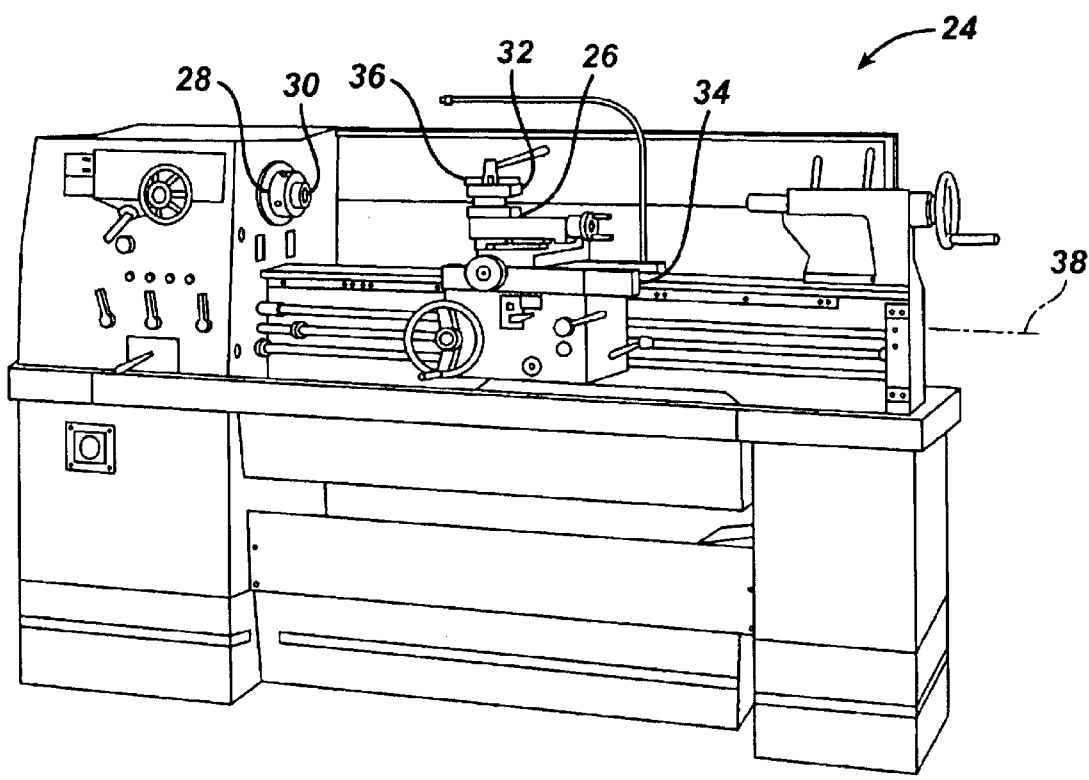
FIG. 4 is a plan view of a turret lathe used in accordance with the method of FIG. 1.

Referring now to FIG. 4, a turning machine 24 that functions in accordance with the present invention is shown. Specifically, this turning machine 24 is a horizontal, chucking-type, turret lathe adapted to be provided with a plurality of cutting tools. The lathe 24 includes a tool feed carriage 26 and a turning motor 28 with a component holding means 30. The component holding means 30 may be provided as a chuck or a collet or any other suitable means known in the art to hold an implant component without deforming the component. Preferably it is a collet or chuck with a fitted recess sized for gripping and supporting the particular component. The tool feed carriage 26 further includes a turret-type tool holder 32 and a tool feed compound 34 for one or more cutting tools 36, and is adapted to move along a z- or longitudinal axis 38 that is parallel to the turning axis of the engine 28 and also to move along a cross-feed direction. Any or all of the components of the turret lathe 24 are adapted to be numerically controlled by computer (not shown). The turret lathe 24 may also be adapted to include vacuum and/or cooling systems to remove swarf and heat generated by the cutting process.

Figure 5:
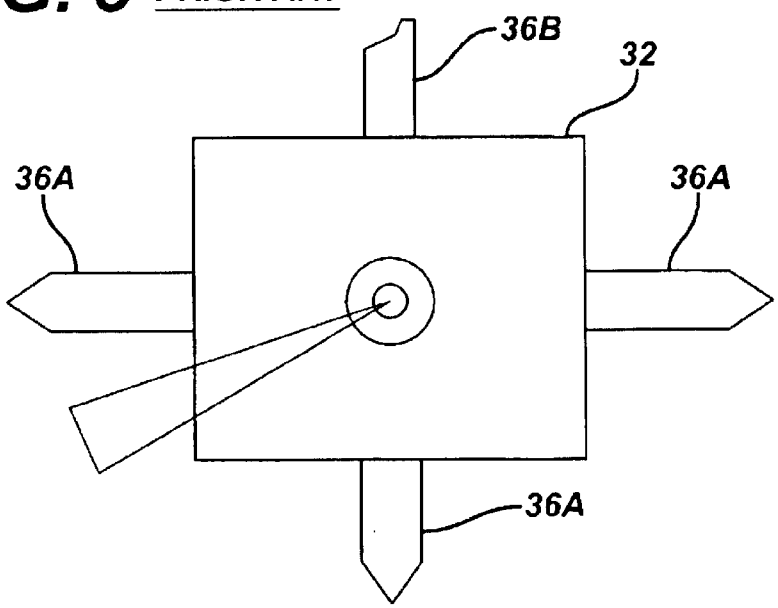
FIG. 5 is a top view of the tool post of the turret lathe of FIG. 4.

Referring now to FIG. 5, a top view of the tool holding assembly 32 of FIG. 4 is shown. A four-way tool turret 32 is shown having four cutting tools 36. Generally all but one of the cutting tools 36 are carbide tools 36A having sharpnesses, radii and rake angles appropriate for the material and shape being cut. However, the invention may be practiced using only the one diamond cutting tool 36B, or with a total number of cutting tools 36 that is greater or less than four while still being able to provide the requisite super finishing characteristics to implant components. The carbide tools, if provided, may be identical tools, with redundant ones serving as replacements to minimize set-up time when one becomes dull; or may be configured to make successively finer passes to reach the desired finish.

Super finishing characteristics are preferably achieved, through computerized numerical control, by cutting the component with one or a plurality of cutting tools 36 such that the component has a circularly symmetric finish region on a surface of the component that is to be subjected to motion and/or sliding against another implant component. If the component is not sufficiently smooth or centered in its raw (e.g. cast, extruded or molded) state, it is first cut to a preliminary contour at which point a different one of the plurality of cutting tools may be moved to cut the surface of the component. Each cutting tool 36 may have a different sharpness and radius. Moreover, a diamond cutting tool 36B should be the last cutting tool to be introduced to the surface of the component, wherein it removes material from the preliminary cut surface to form the final super finished machine cut surface.

One suitable turning machine as described with respect to FIGS. 4 and 5 is Precitech's Nanoform 200 model. The Nanoform 200 model is a two-axis, computer controlled, ultra-precision contouring machine which may be used with diamond cutting tools to form optical quality surfaces on a wide range of materials and which also may be equipped with a high-speed grinding attachment to form precision molds having high quality surfaces. The Nanoform 200 model is built on a granite base and utilizes a passive vibration isolation system. High stiffness hydrostatic oil bearing slideways are arranged in a "T" configuration such that the X-axis (spindle) slide represents the cross-arm of the "T" and the Z-axis (tool holding) slide represents the stem of the "T." The Nanoform 200 model is available with a digital signal processor based control system which provides a one nanometer programming resolution, sub-count feedback signal interpolation and industry standard M and G code programming format.

Figure 6:
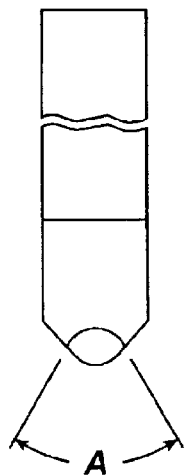
FIG. 6 is a top view of a diamond tool of FIG. 5.
Figure 6A:
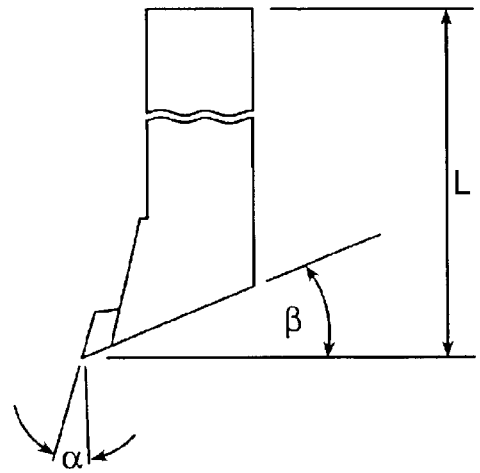
FIG. 6A is a side view of the diamond tool of FIG. 6.

Referring now to FIGS. 6 and 6A, an exemplary diamond cutting tool 36 for surface finishing of UHMWPE surfaces is shown. The tool has a shank length, L, of between about 70 millimeters to about 100 millimeters and an arc, A, of about 140°. Moreover, the exemplary tool has a rake angle, α, of about 5° to about 15° and a front clearance angle, β, of about 30°. One of ordinary skill in the art will appreciate that these measurements may vary from tool to tool and/or may be greater or lesser than the above ranges.

Figure 7:
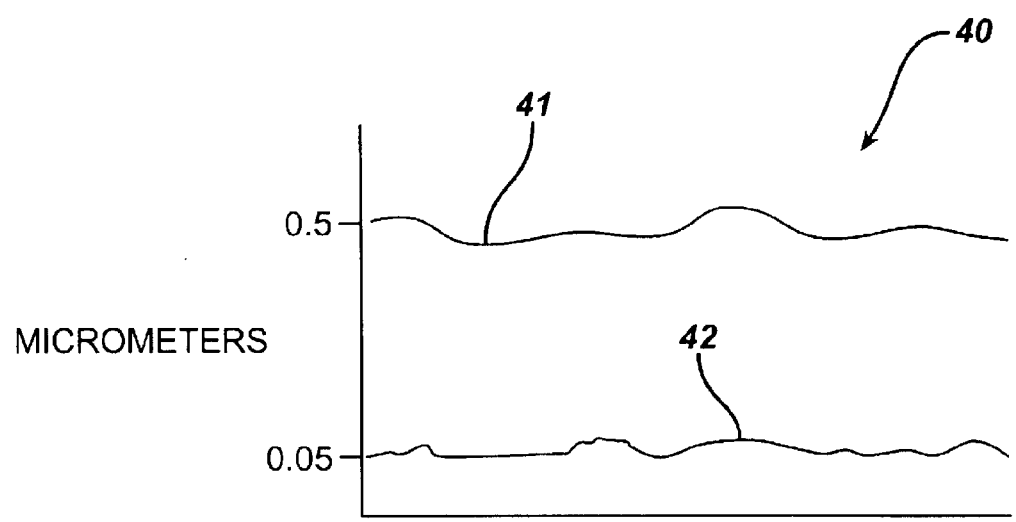
FIG. 7 is a graphical representation of surface roughness characteristics of components prepared according with the process of FIG. 1 versus those prepared in accordance with processes of the prior art.

Referring now to FIG. 7, a graphical representation of surface waviness is shown. The graphical representation 40 notes the surface waviness, in micrometers, of prior art implant components and implant components as they relate to baseline variations of 0.5 and 0.05 micrometers. Prior art implant components have machine cut surface waviness measurements 41 that are greater than about the 0.5 micrometer baseline which corresponds to surface texture that is visible to the unaided eye. These components may be polished to reduce roughness to below 0.4 micrometers, but they will retain this pattern of wavy cut lines. Implant components prepared in accordance with the process of FIG. 1, however, have a surface waviness 42 substantially less than approximately 0.5 micrometers and preferably lying approximately between the 0.05 baseline and 0.1 micrometers, or below. It is the ability of the process of FIG. 1 to provide a smooth surface on implant components with a waviness of less than 0.5 micrometers that greatly reduces or eliminates the formation of wear debris during the "breaking in" or "wearing-in" of the components due to, among other things, micromotion and/or articulation and/or sliding.

Figure 8:
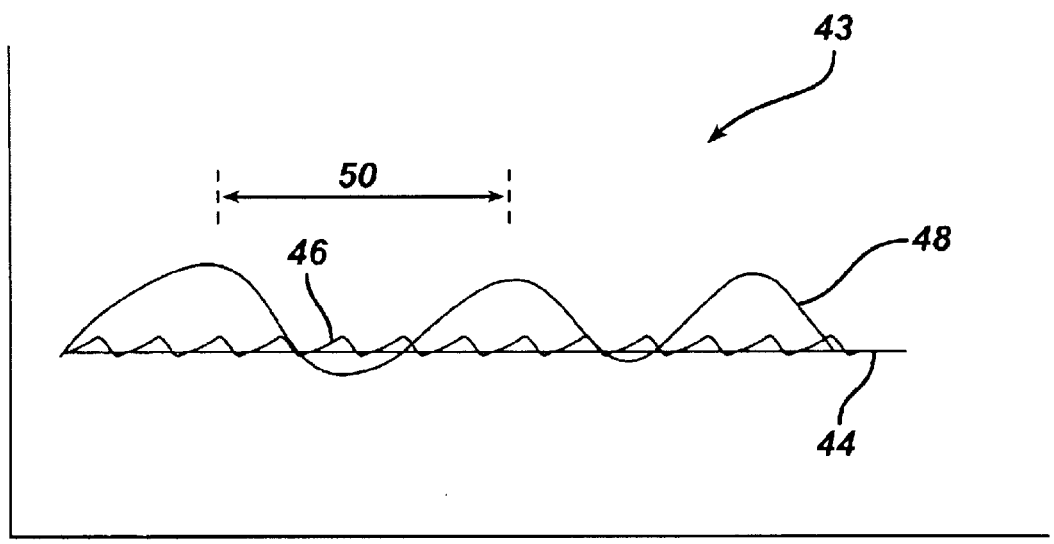
FIG. 8 is a schematic representation of surface flatness or contour of components prepared in accordance with the process of FIG. 1 and of components prepared in accordance with prior art processes.

Referring now to FIG. 8, a schematic representation of surface contour is shown. The schematic representation 43 shows a baseline 44 that corresponds to an ideal flat or spherical surface contour of an implanted component. Curve 48 shows the actual profile and resulting machine ridges produced during a surface cutting and finishing process of the prior art. The prior art residual machine ridges 48 depart greatly from the ideal contour baseline 44 during one period 50 (corresponding to the feed per rotation of the component/tool). Similarly large excursions may occur over even shorter intervals when the prior art cutting tool has waviness or wear irregularities. Conversely, small residual cut artifacts 46 are left by the super finishing cutting process of the present invention which depart from the ideal baseline 44 by a very small amount. That amount of departure is substantially less than 0.5 micrometers, and is not visible to the unaided eye. Surface roughness is similarly very low, even without secondary polishing.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims.

What is claimed is:

1. A method of preparing a contact surface of an implantable prosthetic joint or bone component wherein the contact surface is a polymeric face which is to be subjected to contact or motion during implantation or use, such method comprising the steps of:

mounting the joint or bone component and a cutting tool on a cutting machine, and operating the cutting machine to cut a symmetric surface contour across the polymeric face of the component wherein the cutting tool has an edge contour formed on a radius effective to provide a precise contact point to cut said surface contour with a surface finish substantially smoother than about 0.5 micrometers.

2. The method of claim 1, wherein the contact surface is a load bearing surface.

3. The method of claim 1, wherein the cutting tool includes a diamond mounted in a tool tip insert.

4. The method of claim 3, further comprising the step of:

orienting the tool tip insert in a numerically-controlled tool compound for sweeping said surface contour along a cross-feed profile selected from the group consisting of spherical contour, a cylindrical contour, and a tapered contour.

5. The method of claim 1, further comprising the step of:

driving at least one non-diamond cutting tool along the face with computerized control of tool position along a cross direction to cut a preliminary contour.

6. The method of claim 1, wherein the cutting machine is operated to fly cut a flat surface on the component.

7. The method of claim 1, wherein the cutting tool has a waviness under about 0.5 micrometers.

8. The method of claim 1, wherein the cutting machine operates with air bearings to effectively isolate the component from mechanical vibration during turning.

9. The method of claim 1, wherein the polymeric face is formed of ultra-high molecular weight polyethylene.

10. The method of claim 1, wherein the surface finish of the component is smoother than approximately 0.10 micrometers.

11. The method of claim 1, wherein the step of operating is performed to form said surface contour substantially free of tool marks of a size visible to the unaided eye.

12. The method of claim 1, wherein the cutting machine is a horizontal turret lathe or mill that turns at a rate over one thousand revolutions per minute.

13. The method of claim 1, wherein the cutting tool has a shank length in the range of about 70 millimeters to about 100 millimeters, a rake angle of about 5° to about 15°, a front clearance angle of about 30° and an arc of about 140°.

14. A method of preparing a contact surface of an implantable prosthetic joint or bone component wherein the contact surface is a polymeric face which is to be subjected to contact or motion during implantation or use, such method comprising the steps of:

mounting the joint or bone component and at least one cutting tool on a turret lathe cutting the polymeric face of the component with the at least one cutting tool, and controlling tool position along a cross direction so as to cut a symmetric surface contour across said polymeric face as the turning machine turns wherein the at least one cutting tool has an edge contour formed on a radius effective to provide a precise contact point to form said surface contour with an as-machined surface finish substantially smoother than about 0.5 micrometers.

* * * * *